United States Patent [19]
Crespo et al.

[11] Patent Number: 5,631,279
[45] Date of Patent: May 20, 1997

[54] PERHYDROISOINDOLE DERIVATIVES, PREPARATION THEREOF AND PHARMACEUTICAL COMPOSITIONS CONTAINING SAME

[75] Inventors: Andre Crespo, Ormesson; Veronique Fardin, Saint Maur Des Fosses; Jean-Marc Guillaume, Paris; Jean-Luc Malleron, Marcoussis; Jean-Francois Peyronel, Palaiseau, all of France

[73] Assignee: Rhone-Poulenc Rorer, S.A., Antony, France

[21] Appl. No.: 448,402

[22] PCT Filed: Apr. 1, 1994

[86] PCT No.: PCT/FR94/00371

§ 371 Date: Jun. 7, 1995

§ 102(e) Date: Jun. 7, 1995

[87] PCT Pub. No.: WO94/22822

PCT Pub. Date: Oct. 13, 1994

[30] Foreign Application Priority Data

Apr. 5, 1993 [FR] France .................. 93 03965

[51] Int. Cl.[6] .................. C07D 209/44; A61K 31/40
[52] U.S. Cl. .................. 514/414; 514/298; 514/307; 514/314; 514/339; 514/365; 514/372; 514/374; 514/383; 514/397; 514/416; 546/102; 546/146; 546/175; 546/277.1; 548/181; 548/214; 548/236; 548/267.6; 548/312.1; 548/455; 548/465; 548/470
[58] Field of Search .................. 548/470, 455, 548/465, 181, 214, 236, 267.6, 312.1; 514/414, 416, 298, 307, 314, 339, 365, 372, 374, 383, 397; 546/102, 146, 175, 277.1

[56] References Cited

U.S. PATENT DOCUMENTS 5,102,667  4/1992  Dubroeucq et al. .................. 514/416 X
5,112,988  5/1992  Dubroeucq et al. .................. 548/470
5,451,601  9/1995  Achard et al. .................. 514/416
5,484,804  1/1996  Achard et al. .................. 514/414

FOREIGN PATENT DOCUMENTS 0429366   5/1991   European Pat. Off. .
0430771   6/1991   European Pat. Off. .
0514273   11/1992  European Pat. Off. .
WO92/20654 11/1992  WIPO .
WO92/20653 11/1992  WIPO .
WO93/21155 10/1993  WIPO .
WO93/21154 10/1993  WIPO .

*Primary Examiner*—Jacqueline Haley
*Attorney, Agent, or Firm*—Finnegan, Henderson, Farabow, Garrett & Dunner, L.L.P.

[57] ABSTRACT

This invention relates to perhydroisoindole derivatives of 08/448,402 formula (I), wherein radicals R are phenyl radicals optionally 2-or 3-substituted by a halogen atom or a methyl radical; $R_1$ is optionally substituted phenyl, cyclohexadienyl, naphthyl, indenyl or optionally substituted heterocyclyl; $R_2$ is H, halogen, OH, alkyl, aminoalkyl, alkylaminoalkyl, dialkylaminoalkyl, alkoxy, alkylthio, acyloxy, acyloxy, carboxy, optionally substituted alkyloxycarbonyl, benzyloxycarbonyl, amino or acylamino; and $R_3$ is optionally 2-substituted phenyl; optionally salts thereof where applicable; and preparation thereof. Said derivatives are particularly useful as neurokinin A antagonists.

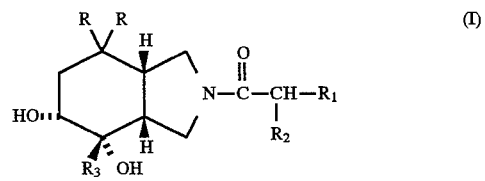

14 Claims, No Drawings

PERHYDROISOINDOLE DERIVATIVES, PREPARATION THEREOF AND PHARMACEUTICAL COMPOSITIONS CONTAINING SAME

This application is a National Stage application of PCT/FR94/00371, filed Apr. 1, 1994 and published as WO94/22822 on Oct. 13, 1994.

DESCRIPTION OF THE INVENTION

The present invention relates to perhydroisoindole derivatives of general formula:

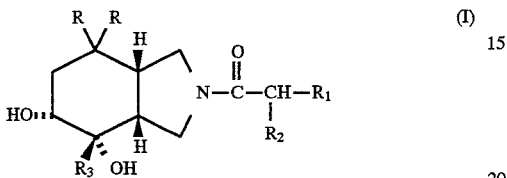

and to their salts when they exist, which antagonize the effects of neurokinin A and are, as a result, particularly advantageous in the therapeutic fields in which this substance is known to be involved.

Neurokinin A is involved in many pathologies, such as pain transmission, arthritis, asthma, inflammatory phenomena, psychosis, vascular tension disorders, vesical disorders, cystisis, etc., which is why the isoindole derivatives of general formula (I) are of considerable value.

The effects of neurokinin A are mainly mediated by the NK2 receptors.

European Patent Application EP 429,366 has described antagonists of substance P of structure:

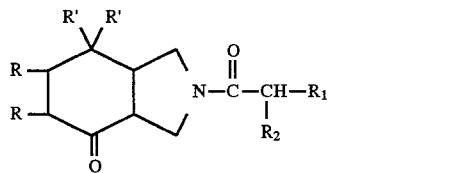

in which the symbols R are hydrogen or together form a bond, the symbols R' are optionally substituted phenyl radicals and the symbols $R_1$ and $R_2$ represent various substitutions. However, these perhydroisoindolone derivatives do not display any antagonistic activity to NK2 receptors.

American Patent No. 4,042,707 has described products derived from the isoindole of general formula:

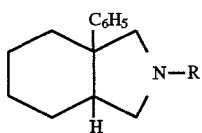

having an opiate activity. These products have no activity towards neurokinin A.

In the general formula (I):
the symbols R are identical and represent phenyl radicals which are optionally substituted with a halogen atom or with a methyl radical in the 2- or 3-position,
the symbol $R_1$ represents a phenyl radical which is optionally substituted with one or more halogen atoms or hydroxyl, benzyloxy or alkyl radicals which may optionally be substituted (with halogen atoms or with amino, alkylamino or dialkylamino radicals) or with alkyloxy or alkylthio radicals which may optionally be substituted [with hydroxyl, amino, alkylamino or dialkylamino radicals which are optionally substituted (with phenyl, hydroxyl or amino radicals), or dialkylamino radicals whose alkyl portions form, with the nitrogen atom to which they are attached, a 5- to 6-membered heterocycle which may contain another hetero atom chosen from oxygen, sulphur or nitrogen, and optionally substituted with an alkyl, hydroxyl or hydroxyalkyl radical], or substituted with amino, alkylamino or dialkylamino radicals whose alkyl portions may form, together with the nitrogen atom to which they are attached, a heterocycle as defined above, or represents a cyclohexadienyl, naphthyl or indenyl radical, or a saturated or unsaturated mono- or polycyclic heterocyclic radical containing 5 to 9 carbon atoms and one or more hetero atoms chosen from oxygen, nitrogen or sulphur, and optionally substituted with a halogen atom or with an alkyl, alkyloxy, aminoalkyl, alkylaminoalkyl or dialkylaminoalkyl radical, the symbol $R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, and the symbol $R_3$ represents a phenyl radical which is optionally substituted in the 2-position with an alkyl or alkyloxy radical containing 1 or 2 carbon atoms.

It is understood that the alkyl or acyl radicals cited above contain (except where especially mentioned) 1 to 4 carbon atoms in a straight or branched chain.

When R carries a halogen substituent, the latter may be chosen from chlorine or fluorine.

When $R_1$ contains a halogen atom, the latter may be chosen from chlorine, bromine, fluorine or iodine.

When $R_1$ represents a saturated or unsaturated mono- or polycyclic heterocyclic radical, it may, by way of example, be chosen from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl or naphthyridinyl.

When $R_1$ represents phenyl substituted with a chain carrying a heterocycle, the latter may be chosen from pyrrolidinyl, morpholino, piperidyl, tetrahydropyridyl, piperazinyl or thiomorpholino.

When the symbol $R_2$ is other than a hydrogen atom, the substituted chain on the isoindole has a chiral center, and it is understood that the (R) or (S) stereoisomeric forms and their mixtures form part of the present invention.

Moreover, the (3aRS,4RS,5RS,7aRS) racemic forms of the perhydroisoindole derivatives of general formula (I) also display an antagonistic activity to neurokinin A. Their application to the preparation of a medicament intended for the treatment of complaints mediated by the NK2 tachykinin receptor also enter into the scope of the present invention.

According to the invention, the perhydroisoindole derivatives of general formula (I) may be obtained by the action of the acid of general formula:

or of a reactive derivative of this acid, in which $R_1$ and $R_2$ are defined as above, on an isoindole derivative of general formula:

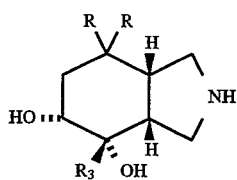

(III)

in which the symbols R and $R_3$ are defined as above.

It is understood that the amino, alkylamino or carboxyl radicals contained in $R_1$ and/or $R_2$ are preferably protected beforehand. The protection is performed by any compatible group, whose installation and removal do not affect the remainder of the molecule. The protection is in particular performed according to the methods described by T. W. Greene, Protective Groups in Organic Synthesis, A. Wiley—Interscience Publication (1981), or by McOmie, Protective Groups in Organic Chemistry, Plenum Press (1973).

By way of example, the amino or alkylamino groups may be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl or acetyl radicals or by benzyloxycarbonyl or its substituted derivatives;

the acidic groups may be protected by methyl, ethyl, t-butyl, benzyl, substituted benzyl or benzhydryl radicals.

In addition, when $R_2$ represents a hydroxyl radical, it is preferable to protect this radical beforehand. The protection is for example performed by an acetyl, trialkylsilyl or benzyl radical, in the form of a carbonate by a radical —COORa in which Ra is an alkyl or benzyl radical, or in the form of a ketone.

When the condensation of a reactive derivative of the acid of general formula (II) is carried out, the process is advantageously performed using the acid chloride, the anhydride, a mixed anhydride or a reactive ester in which the ester residue is a succinimido, optionally substituted 1-benzotriazolyl, 4-nitrophenyl, 2,4-dinitrophenyl, pentachlorophenyl or phthalimido radical.

The reaction is generally carried out at a temperature between –40° and +40° C., in an organic solvent such as a chlorinated solvent (dichloromethane, dichloroethane or chloroform for example), a hydrocarbon (toluene for example), an ether (tetrahydrofuran or dioxane for example), an ester (ethyl acetate for example), an amide (dimethylacetamide or dimethylformamide for example), or a ketone (acetone for example) or in a mixture of these solvents, in the presence of an acid acceptor such as a nitrogen-containing organic base such as, for example, pyridine, dimethylaminopyridine, N-methylmorpholine or a trialkylamine (in particular diisopropylethylamine or triethylamine) or such as an epoxide (propylene oxide for example). It is also possible to perform the process in the presence of a condensing agent such as a carbodiimide [for example dicyclohexylcarbodiimide or 1-(3-dimethylaminopropyl)-3-ethylcarbodiimide], N,N'-carbonyldiimidazole or 2-ethoxy-1-ethoxycarbonyl-1,2-dihydroquinoline or alternatively in an aqueous-organic medium, in the presence of an alkaline condensing agent such as sodium bicarbonate.

According to the invention, the perhydroisoindole derivatives for which $R_1$ is a phenyl radical which is substituted with a hydroxyl radical may also be obtained by conversion of a perhydroisoindole derivative for which $R_1$ is a phenyl radical which is substituted with a benzyloxy radical, by any known method which does not affect the remainder of the molecule.

Any known method for the removal of a benzyl radical is performed, for example catalytic hydrogenation in the presence of a catalyst such as palladium hydroxide at a temperature between 40° and 80° C., in an organic solvent such as an alcohol for example. It is optionally possible to perform the process under pressure (1 to 30 atmospheres).

According to the invention, the perhydroisoindole derivatives for which $R_1$ is an amino-substituted phenyl radical may also be obtained by conversion of a perhydroisoindole derivative according to claim 1 for which $R_1$ is a phenyl radical which is substituted with a nitro radical by any known reduction method which does not affect the rest of the molecule.

The reduction is in particular carried out in the presence of zinc in an aqueous-alcoholic medium.

The acids of general formula (II) may be prepared according to the methods described below in the examples, according to the methods described in Patent Application EP 429,366 or by analogy with these methods.

The perhydroisoindole derivative of general formula (III) may be obtained by the action of an organometallic compound of general formula:

$$R_3\text{-M} \qquad (IV)$$

in which $R_3$ is defined as above, and M represents lithium, or a radical MgX or $CeX_2$ for which X is a halogen atom, on the corresponding perhydroisoindolone derivative of general formula:

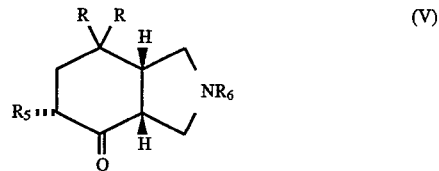

(V)

in which R is defined as above, $R_5$ is an optionally protected hydroxyl radical and $R_6$ is a protecting radical, followed by release of the protecting radical from $R_5$ and removal of the protecting radical $R_6$.

The protecting radical $R_6$ may be any amino-protecting group which is compatible with the reaction and whose installation and removal does not alter the remainder of the molecule. Alkyloxycarbonyl, benzyloxycarbonyl, optionally substituted benzyl, formyl, chloroacetyl, trichloroacetyl, trifluoroacetyl, vinyloxycarbonyl, phenoxycarbonyl, 1-chloroethoxycarbonyl or chlorocarbonyl groups may be mentioned by way of example.

The reaction is carried out in an anhydrous medium, under the usual conditions for the reaction of organometallic compounds with a ketone, which do not affect the remainder of the molecule. The procedure is in particular performed in an ether (for example tetrahydrofuran or diethyl ether) optionally in the presence of anhydrous cerium chloride at a temperature between –78° and 30° C. It is understood that, depending on the nature of the protecting radical of the radical $R_5$, the latter may be removed simultaneously in the reaction.

The subsequent removal of the protecting radical $R_6$ is carried out according to the usual methods. In particular according to the methods described by T. W. Greene, by A. Wiley or by McOmie in the references cited above.

The perhydroisoindolone derivative of general formula (V) for which $R_5$ is a previously protected hydroxyl radical may be prepared by analogy with the method described in the European Patent Application EP 429,366, or as described below in the examples.

It is understood that the perhydroisoindole derivatives of general formulae (I), (III) and (V) may have several stereoisomeric forms. In order to obtain a product of general formula (I) of (3aR,7aR) form, the separation of the isomeric forms is preferably carried out on the derivative of general formula (III) or on another intermediate carrying an oxo radical in the 4-position. The separation is carried out according to any known method which is compatible with the molecule.

By way of example, the separation may be carried out by preparation of an optically active salt, by the action of L(+)- or D(−)-mandelic acid, ditoluoyltartaric acid or dibenzoyltartaric acid, followed by separation of the isomers by crystallization. The desired isomer is released from its salt in basic medium.

The isoindole derivatives of general formula (I) may be purified, where appropriate, by physical methods such as crystallization or chromatography.

Where appropriate, the derivatives of general formula (I) for which the symbols $R_1$ and/or $R_2$ contain amino or alkylamino substituents, and the derivatives of general formula (III), may be converted to addition salts with acids. Examples of addition salts with pharmaceutically acceptable acids which may be mentioned are salts formed with inorganic acids (hydrochlorides, hydrobromides, sulphates, nitrates or phosphates) or with organic acids (succinates, fumarates, tartrates, acetates, propionates, maleates, titrates, methanesulphonates, p-toluenesulphonates or isethionates, or with substitution derivatives of these compounds).

When $R_2$ represents a carboxyl radical, the isoindole derivatives of general formula (I) may also, where appropriate, be converted to metal salts or to addition salts with a nitrogen-containing base, according to methods known per se. These salts may be obtained by the action of a metallic base (for example an alkali or alkaline-earth metal base), ammonia or an amine, on a product according to the invention, in an appropriate solvent such as an alcohol, an ether or water, or by exchange reaction with a salt of an organic acid. The salt formed precipitates after optional concentration of the solution, and it is separated out by filtration, decantation or freeze-drying. Examples of pharmaceutically acceptable salts which may be mentioned are salts with alkali metals (sodium, potassium or lithium) or with alkaline-earth metals (magnesium or calcium), the ammonium salt or salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The isoindole derivatives of general formula (III) and their salts are new products which are also endowed with antagonistic activity to effects of neurokinin A.

Neurokinin A is known to be involved in a certain number of pathological fields such as asthma, pain transmission, headaches, migraine, inflammatory phenomena, arthritis, neurodegenerative mental disorders, neurological disorders, vascular tension disorders, vesical disorders, cystitis, and painful and hypersecretory spasmodic conditions of the digestive system [C. A. Maggi et al., Drugs of the Future; 18(2), 155–158 (1993); C. A. Maggi et al., J. Auton. Pharmacol., 13, 23–93 (1993)].

The isoindole derivatives according to the present invention, as well as their (3aRS,4RS,5RS,7aRS) racemic forms and the isoindole derivatives of general formula (III), may find an application in the fields in which neurokinin A is involved.

In effect, the products according to the invention display an affinity for the neurokinin A receptors at concentrations of between 10 and 1000 nM ($IC_{50}$) demonstrated in the following technique: Evaluation of the affinity for human $NK_2$ receptor:

The affinity of the products for human $NK_2$ receptor was evaluated on a washed homogenate of insect cells (Spodoptera frugiperda, SF21) expressing the $NK_2$ receptor cloned from the human jejunum. The expression of this receptor in the SF21 line is obtained by infection of the cells using a recombinant baculovirus (BVE-h$NK_2$) which possesses the gene of the $NK_2$ receptor studied. The affinity of the products was measured by studying the possible inhibition of the specific binding of neurokinin A labelled with iodine-125 ($^{125}$I-iodohistidyl NKA) on these cell homogenates by various concentrations of product. The binding of iodinated NKA, in the absence or presence of product to be evaluated, is measured by counting the radioactivity on a gamma counter after incubation for 60 minutes at 25° C. in the presence of 0.1 nM radioactive ligand and rapid filtration of the incubation medium under reduced pressure. The non-specific binding is defined in the presence of 5 µM of non-radioactive NKA. The concentration of product which inhibits the specific binding of the ligand by 50 % ($IC_{50}$) is determined by non-linear regression, using the calculation program of G. A. McPherson, Analysis of radioligand binding experiments, A collection of computer programs for the IBM PC. J. Pharmacol., Neth., 14, 213–228 (1985).

The in vitro antagonistic activity of the products is determined with respect to rabbit pulmonary artery contractions induced by [Lys$^5$MeLeu$^9$Nle$^{10}$]NKA(4–10) according to the technique described by D. Regoli et al., Trends Pharmacol. Sci, 2, 290–295 (1988) and P. D'Orléans-Juste et al., Eur. J. Pharmacol., 125, 37–44 (1985). The pulmonary artery of the rabbit (male, New Zealand albino) is withdrawn; the endothelium is destroyed by introduction into the arterial lumen of a glass rod coated with filter paper, and the artery is then cut into rings and incubated in an isolated-organ tank containing an oxygenated Krebs solution (95% $O_2$; 5% $CO_2$) at 37° C. at a tension of 1 g. After determining the agonistic activity of [Lys$^5$MeLeu$^9$Nle$^{10}$]NKA(4–10) (contractile effect), the product to be studied is incubated for 2 hours in the isolated-organ tank before a further addition of [Lys$^5$MeLeu$^9$Nle$^{10}$]NKA(4–10). The percentage inhibition obtained is calculated. The antagonistic activity of a product is expressed in terms of $IC^{50}$.

In the above technique, the products studied display an antagonism to rabbit pulmonary artery contractions at the following concentration:

| Product studied | $IC_{50}$ (nM) |
| --- | --- |
| Example 1 | 215 |

Finally, the isoindole derivatives according to the present invention have no toxicity; they revealed themselves to be non-toxic in mice at a dose of 40 mg/kg via the subcutaneous route.

The isoindole derivatives according to the invention, corresponding to the general formula (I) or (III), are also very advantageous because of the synergy which they provide when they are combined with products which are endowed with an antagonistic activity to NK1 receptors.

NK1 receptor antagonists (antagonists to the effects of substance P) are known and in particular described in Patent Applications EP 429,366, EP 514,273, EP 514,275, WO 90/05525, WO 90/05729, WO 91/18899, WO 91/09844, WO 92/01688, WO 92/06079, WO 92/15585, WO 92/12151, WO 92/20661, WO 92/20676, WO 92/21677, WO 93/00330, WO 93/00331, WO 93/01159, WO 93/01169, WO 93/01165, WO 93/01170, WO 93/06099, WO 93/09116, WO 93/10073, WO 93/18023, WO 93/19064, WO 93/21155, WO 93/21181, WO 93/23380, EP 499,313 EP 394,989, EP 443,132, EP 482,539, EP 512,902, EP 517,589, EP 520,555, EP 522,808, EP 528,495, EP 532,456, EP 533,280, EP 536,817, EP 545,478, EP 559,538, XIIth Int. Symp. on Med. Chem., Basle, 13–17 September 1992 or 3rd Meeting of the European Neuropeptide Club (Cambridge 5–7 April 1993). Such products may be combined with the products according to the invention, thereby making it possible to obtain a potentialization of the antagonistic effects of the NK1 and NK2 receptors.

EXAMPLES

The examples which follow, given without any limitation being implied, illustrate the present invention.

Example 1 RPR106145

To a solution of 0.5 g of (3aR,4R,5R,7aR)-7,7-diphenyl-4-(2-methoxyphenyl)perhydro-4,5-isoindolediol and 0.23 g of 3-indolylacetic acid in 50 cm$^3$ of dichloromethane, cooled to 0° C., are added 5 mg of 1-hydroxybenzotriazole hydrate, 0.28 g of 1-(3-dimethylaminopropyl)-3-ethylcarbodiimide and 0.24 cm$^3$ of diisopropylethylamine. The mixture is stirred for 2 hours at 0° C. and for 1 hour at room temperature, followed by addition of 25 cm$^3$ of water. The organic phase is separated off after settling, dried over magnesium sulphate and concentrated to dryness under reduced pressure (2.7 kPa). The yellow crystals obtained are chromatographed on a column of Merck silica gel (particle size 0.04–0.06 mm, diameter 1.5 cm, height 30 cm), eluting under a nitrogen pressure of 50 kPa with ethyl acetate and collecting 25 cm$^3$ fractions. Fractions 4 to 8 are combined and then concentrated to dryness under reduced pressure (2.7 kPa). The solid obtained is crystallized in 5 cm$^3$ of isopropyl ether. 0.58 g of (3aR, 4R, 5R,7aR)-7,7-diphenyl-4-(2-methoxyphenyl)-2-[(3-indolylacetyl]perhydro-4,5-isoindolediol is obtained, melting at 218°–220° C.

(3aR,4R,5R,7aR)-7,7-Diphenyl-4-(2-methoxyphenyl)perhydro-4,5-isoindolediol may be obtained in the following way:

To 2.3 g of (3aR,4R, 5R,7aR)-7,7-diphenyl-4-(2-methoxyphenyl)perhydro-4,5-isoindolediol D-1,4-ditoluoyltartrate dissolved in 46 cm$^3$ of methanol are added 100 cm$^3$ of water and 6 cm$^3$ of aqueous 1N sodium hydroxide; the reaction mixture is stirred at room temperature until the starting product has disappeared. The crystals formed are filtered, filtered off and then crystallized in 20 cm$^3$ of isopropyl ether. 1.4 g of (3aR,4R,5R,7aR)-7,7-diphenyl-4-(2-methoxyphenyl)perhydro-4,5-isoindolediol are obtained, melting at 183°–185° C.

(3aR,4R,5R,7aR)-7,7-Diphenyl-4-(2-methoxyphenyl)perhydro-4,5-isoindolediol D-1,4-ditoluoyltartrate may be prepared in the following way:

To a solution of 7.5 g of (3aRS,4RS,5RS,7aRS)-7,7-diphenyl-4-(2-methoxyphenyl)perhydro-4,5-isoindolediol in 75 cm$^3$ of methanol are added, with stirring, 7.3 g of (+)-D-1,4-ditoluoyltartaric acid. After total dissolution, the reaction mixture is concentrated to dryness under reduced pressure (2.7 kPa); the meringue-like product obtained is crystallized a first time in 100 cm$^3$ of acetonitrile and then a second time in 400 cm$^3$ of acetonitrile. The crystals obtained are recrystallized to a constant optical rotation in a mixture of ethanol and water (60/40 by volume). 2.3 g of (3aR,4R,5R,7aR)-7,7-diphenyl-4-(2-methoxyphenyl)perhydro-4,5-isoindolediol D-1,4-ditoluoyltartrate are obtained, melting at 240° C.

(3aRS,4RS,5RS,7aRS)-7,7-Diphenyl-4-(2-methoxyphenyl)perhydro-4,5-isoindolediol may be prepared in the following way:

A mixture of 2 g of (3aRS, 4RS, 5RS, 7aRS)-2-benzyl-7,7-diphenyl-4-(2-methoxyphenyl)perhydro-4,5-isoindolediol and 50 cm$^3$ of ethanol is heated to 65° C. with stirring; 0.65 g of 20% palladium hydroxide on charcoal is added, and the reaction mixture is then hydrogenated, with stirring, at a temperature of 65° C. and at atmospheric pressure. After reaction for 1 hour, the theoretical volume of hydrogen has been absorbed; the reaction mixture is filtered and then concentrated to dryness under reduced pressure (2.7 kPa). The residue is crystallized in 10. cm$^3$ of isopropyl ether. 1.45 g of (3aRS,4RS,5RS,7aRS)-7,7-diphenyl-4-(2-methoxyphenyl)perhydro-4,5-isoindolediol are obtained, melting at 230° C.

(3aRS,4RS,5RS,7aRS)-2-Benzyl-7,7-diphenyl-4-(2-methoxyphenyl)perhydro-4,5-isoindolediol may be prepared in the following way:

To a suspension of 84.4 g of 2-methoxyphenylmagnesium bromide in 1000 cm$^3$ of tetrahydrofuran is added dropwise, at room temperature and with stirring, a solution of 22 g of (3aRS,5RS,7aRS)-5-acetoxy-2-benzyl-7,7-diphenylperhydro-4-isoindolone in 220 cm$^3$ of tetrahydrofuran. The reaction mixture is stirred at room temperature for 18 hours, treated with 200 cm$^3$ of saturated aqueous ammonium chloride solution, and taken up with 200 cm$^3$ of diethyl ether and 200 g of ice. The organic phase is separated off after settling, dried over magnesium sulphate, filtered and concentrated to dryness under reduced pressure (2.7 kPa). The residue is crystallized in 250 cm$^3$ of petroleum ether and then recrystallized in 200 cm$^3$ of methanol; the crystals are washed with 200 cm$^3$ of isopropyl ether. 16.4 g of (3aRS,4RS,5RS,7aRS)-2-benzyl-7,7-diphenyl-4-(2-methoxyphenyl)perhydro-4,5-isoindolediol are obtained, melting at 236° C.

(3aRS,5RS,7aRS)-5-Acetoxy-2-benzyl-7,7-diphenylperhydro-4-isoindolone may be prepared in the following way:

To a solution of 86 g of 6-acetoxy-4,4-diphenyl-2-cyclohexenone and 96 cm$^3$ of N-butoxymethyl-N-(trimethylsilylmethyl)benzylamine in 1000 cm$^3$ of dichloromethane are added 15 drops of trifluoroacetic acid. The reaction mixture is stirred at room temperature for 15 hours, followed by addition of 2 g of sodium carbonate and concentration to dryness under reduced pressure (2.7 kPa). The residue is chromatographed on a column of Merck silica gel (particle size 0.04–0.06 mm, diameter 7 cm, height 70 cm), eluting under a nitrogen pressure of 50 kPa with a mixture of cyclohexane and ethyl acetate (20/80 by volume) and collecting 200 cm$^2$ fractions. Fractions 6 to 10 are combined and concentrated to dryness under reduced pressure (2.7 kPa). 70 g of (3aRS,5RS,7aRS)-5-acetoxy-2-benzyl-7,7-diphenylperhydro-4-isoindolone in the form of a syrup are obtained (melting point below 40° C.).

N-Butoxymethyl-N-(trimethylsilylmethyl)benzylamine may be prepared according to the method of Y. Terao et al., Chem. Pharm. Bull., 33, 2762 (1985).

6-Acetoxy-4,4-diphenyl-2-cyclohexenone may be prepared according to the method described by W. Oppolzer et al., Helv. Chim. Acta, 59, 2012 (1976).

Example 2 RPR102862

To a solution of 0.1 g of (3aR,4R,5R,7aR)-7,7-diphenyl-4-(2-methoxyphenyl)perhydro-4,5-isoindolediol and 0.05 g of (S)-2-(2-methoxyphenyl)propanoic acid in 5 cm³ of dichloromethane, cooled to 0° C., are added 5 mg of 1-hydroxybenzotriazole hydrate, 0.06 g of 1-(3-dimethylaminopropyl)-3-ethylcarbodiimide and 0.04 cm³ of diisopropylethylamine. The mixture is stirred for 4 hours at room temperature, followed by addition of 30 cm³ of water, 10 cm³ of saturated aqueous sodium bicarbonate solution and 50 cm³ of saturated aqueous sodium chloride solution. The organic phase is separated off after settling, dried over magnesium sulphate and concentrated to dryness under reduced pressure (2.7 kPa). The yellow residue obtained is chromatographed on a column of Merck silica gel (particle size 0.04–0.06 mm, diameter 1.5 cm, height 30 cm), eluting under a nitrogen pressure of 50 kPa with a mixture of cyclohexane and ethyl acetate (60/40 by volume) and collecting 10 cm³ fractions. Fractions 8 to 13 are combined and then concentrated to dryness under reduced pressure (2.7 kPa). 0.08 g of (3aR, 4R, 5R, 7aR)-7,7-diphenyl-4-(2-methoxyphenyl)-2[(S)-2-(2-methoxyphenyl)propionyl]perhydro-4,5-isoindolediol is obtained, melting at 172° C.

(S)-2-(2-Methoxyphenyl)propionic acid may be prepared, by analogy with the methods described by D. A. Evans et al., Tetrahedron, 44, 5525, (1988), according to the following procedure:

To a solution, cooled to +5° C., of 4.1 g of (4S, 5S)-4-methyl-5-phenyl-3-(S)-2-(2-methoxyphenyl)propionyl]-2-oxazolidinone in 60 cm³ of tetrahydrofuran and 30 cm³ of water are added 1.52 g of lithium hydroxide. The reaction mixture is stirred for 3 hours at this temperature and, after returning to room temperature, ethyl acetate is then added, the phases are separated after settling, and the aqueous phase is acidified with 1N aqueous hydrochloric acid solution and extracted with ethyl acetate, and the organic phase is dried over magnesium sulphate and concentrated to dryness under reduced pressure (2.7 kPa). The solid obtained is recrystallized in hexane, filtered off and dried. 0.4 g of 2-(2-methoxyphenyl)-(S)-propionic acid is obtained, in the form of white crystals melting at 102° C. $[\alpha]_D^{20}$=+84.6° (c=1CHCl₃)

(4S, 5S)-4-Methyl-5-phenyl-3-[(S)-2-(2-methoxyphenyl)propionyl]-2-oxazolidinone may be obtained in the following way:

To a solution, cooled to –50° C., of 10 g of (4S,5S)-4-methyl-5-phenyl-3-[(2-methoxyphenyl)acetyl]-2-oxazolidinone in 150 cm³ of tetrahydrofuran are added 19.1 g of sodium 1,1,1,3,3,3-hexamethyldisilazide, and the mixture is stirred for 45 minutes at this temperature, followed by addition of 7.72 cm³ of methyl iodide. The reaction mixture is subsequently stirred for 15 hours at room temperature, and then diluted with ethyl acetate and washed with 50 cm³ of water followed by 50 cm³ of saturated aqueous sodium chloride solution, dried over magnesium sulphate and concentrated to dryness under reduced pressure (2.7 kPa). The residue obtained is crystallized in isopropyl ether, filtered off and dried. 4.2 g of (4S,5S)-4-methyl-5-phenyl-3-[(S)-2-(2-methoxyphenyl)propionyl]-2-oxazolidinone are obtained, in the form of a white solid.

(4S,5S)-4-Methyl-5-phenyl-3-[(2-methoxyphenyl)acetyl]-2-oxazolidinone may be obtained in the following way:

To a suspension of 1.89 g of sodium hydride (80% dispersion in petroleum jelly) in 200 cm³ of dry tetrahydrofuran are added at room temperature 9.38 g of 2-methoxyphenylacetic acid. This suspension is cooled to –30° C. and 7.77 cm³ of pivalolyl chloride are added, finally followed by addition of a solution cooled to –78° C. obtained by adding 35.27 cm³ of a 1.6M solution of butyllithium in hexane to a solution, cooled to –78° C., of 10 g of (4S,5S)-4-methyl-5-phenyl-2-oxazolidinone in 200 cm³ of dry tetrahydrofuran. The reaction mixture is stirred for 45 minutes at –30° C., followed, after returning to room temperature, by addition of 200 cm³ of saturated aqueous ammonium chloride solution, and then 500 cm³ of ethyl acetate; after separation of the phases by settling, the organic phase is washed twice with 100 cm³ of water, then twice with 100 cm³ of saturated aqueous sodium chloride solution, and dried over magnesium sulphate and concentrated to dryness under reduced pressure (2.7 kPa). The residue is chromatographed on a column of silica gel (particle size 0.04–0.06 mm, diameter 4.8 cm, height 36 cm), eluting under a nitrogen pressure of 0.6 bar with a mixture of cyclohexane and ethyl acetate (85/15 and then 80/20 by volume) and collecting 50 cm³ fractions. Fractions 14 to 31 are combined and concentrated to dryness under reduced pressure (2.7 kPa). 13.6 g of (4S,5S)-4-methyl-5-phenyl-3-[(2-methoxyphenyl)acetyl]-2-oxazolidinone are obtained, in the form of a yellow oil.

Example 3 RPR107539

By working according to the procedure of Example 1, starting from 0.2 g of (3aR,4R,5R,7aR)-7,7-diphenyl-4-(2-methoxyphenyl)perhydro-4,5-isoindolediol and 0.11 g of (R)-2-(2-methoxyphenyl) propionic acid, 0.12 g of (3aR,4R, 5R,7aR)-7,7-diphenyl-4-(2-methoxyphenyl)-2-[(R)-2-(2-methoxyphenyl) propionyl]perhydro-4,5-isoindolediol is obtained, melting at 178°–180° C.

(R)-2-(2-methoxyphenyl)propionic acid may be prepared, by analogy with the methods described by D. A. Evans et al., Tetrahedron, 44, 5525, (1988), according to the following procedure:

To a solution, cooled to +5° C., of 10.88 g of (4R, 5R)-4-methyl-5-phenyl-3-[(R)-2-(2-methoxyphenyl)propionyl]-2-oxazolidinone in 300 cm³ of tetrahydrofuran and 100 cm³ of water are added 2.71 g of lithium hydroxide and 13 cm³ of aqueous 30% hydrogen peroxide solution. The reaction mixture is stirred for 3 hours at this temperature, followed, after returning to room temperature, by addition of aqueous sodium sulphite solution and then dichloromethane, and the phases are separated after settling. The aqueous phase is acidified with 4N aqueous hydrochloric acid solution and extracted with dichloromethane, and the organic phase is then dried over magnesium sulphate and concentrated to dryness under reduced pressure (2.7 kPa). The solid obtained is recrystallized in hexane, filtered off and dried. 5.24 g of (R)-2-(2-methoxyphenyl)propionic acid are obtained, in the form of white crystals melting at 102° C.; $[\alpha]_D^{20}$=–76° (c=1; methanol).

(4R, 5R)-4-Methyl-5-phenyl-3-[(R)-2-(2-methoxyphenyl)propionyl]-2-oxazolidinone may be prepared in the following way:

To a solution, cooled to –50° C., of 22.82 g of (4R, 5R)-4-methyl-5-phenyl-3-[(2-methoxyphenyl)acetyl]-2-oxazolidinone in 190 cm³ of tetrahydrofuran are added 19.31 g of sodium 1,1,1,3,3,3-hexamethyldisilazide, and the mixture is stirred for 45 minutes at this temperature, followed by addition of 8.82 cm³ of methyl iodide. The reaction mixture is subsequently stirred for 15 hours at room temperature, and then 18.65 cm³ of acetic acid are added, and the mixture is diluted with 200 cm³ of ethyl acetate and washed with 200 cm³ of water and then with 250 cm³ of saturated aqueous sodium chloride solution, and dried over magnesium sulphate and concentrated to dryness under reduced pressure (2.7 kPa). The residue obtained is crystallized in isopropyl ether, filtered off and dried. 10.95 g of (4R, 5R)-4-methyl-5-phenyl-3-[(R)-2-(2-methoxyphenyl) propionyl]-2-oxazolidinone are obtained, in the form of a white solid melting at 110° C.

(4R, 5R)-4-Methyl-5-phenyl-3-(2-methoxyphenylacetyl)-2-oxazolidinone may be prepared in the following way:

To a solution of 27.4 g of (4R,5R)-4-methyl-5-phenyl-2-oxazolidinone in 200 cm³ of dry tetrahydrofuran are added, at −78° C., 100 cm³ of a 1.6M butyllithium solution in hexane, followed by addition of 33.12 g of a solution of 2-methoxyphenylacetic acid in 30 cm³ of tetrahydrofuran. The mixture is stirred for 30 minutes at this temperature and then allowed to return to room temperature. 200 cm³ of saturated aqueous ammonium chloride solution are subsequently poured in, followed by 200 cm³ of ethyl acetate. The organic phase is washed three times with 300 cm³ of water, and then with 300 cm³ of saturated aqueous sodium chloride solution, and dried over magnesium sulphate and concentrated to dryness under reduced pressure (2.7 kPa). The residue is taken up in 100 cm³ of diethyl ether. 35.5 g of (4R,5R)-4-methyl-5-phenyl-3-[(2-methoxyphenyl)acetyl]-2-oxazolidinone are obtained, in the form of white crystals melting at 126° C.

Example 4 RPR107587

By working according to the experimental procedure of Example 1, starting from 2 g of (3aR,4R,5R,7aR)-7,7-diphenyl-4-(2-methoxyphenyl)perhydro-4,5-isoindolediol and 1.3 g of 2-(benzyloxyphenyl)acetic acid, after purification by chromatography on a column of Merck silica gel (particle size 0.04–0.06 mm, diameter 2 cm, height 28 cm), and eluting under a pressure of 0.5 bar with a mixture of dichloromethane and methanol (97.5/2.5 by volume), 1.1 g of (3aR,4R,5R,7aR)-7,7-diphenyl-4-(2-methoxyphenyl)-2-[(2-benzyloxyphenyl)acetyl]perhydro-4,5-isoindolediol are obtained, melting at 176° C.

Example 5 RPR107588

A mixture of 1.5 g of (3aR,4R, SR,7aR)-7,7-diphenyl-4-(2-methoxyphenyl)-2-[(2-benzyloxyphenyl)acetyl] perhydro-4,5-isoindolediol and 50 cm³ of ethanol is heated to 60° C. with stirring; 0.5 g of 20% palladium hydroxide on charcoal is added and the reaction mixture is then hydrogenated, with stirring, at a temperature of 60° C. and at atmospheric pressure. After reaction for 45 minutes, the theoretical volume of hydrogen has been absorbed; the reaction mixture is filtered, followed by concentration to dryness under reduced pressure (2.7 kPa). The meringue-like product obtained is purified by crystallization in 10 cm³ of isopropyl ether to give 1.09 g of (3aR,4R,5R,7aR)-7,7-diphenyl-4-(2-methoxyphenyl)-2-[(2-hydroxyphenyl)acetyl]perhydro-4,5-isoindolediol, melting at 188° C.

Example 6 RPR108208

By working as in Example 1, starting from 0.62 g of (3aR,4R,5R,7aR)-7,7-diphenyl-4-(2-methoxyphenyl) perhydro-4,5-isoindolediol and 0.30 g of (2-dimethylamino) phenylacetic acid, 0.35 g of (3aR,4R,5R,7aR)-7,7-diphenyl-4-(2-methoxyphenyl)-2-[(2-dimethylaminophenyl)acetyl] perhydro-4,5-isoindolediol is obtained, melting at 175°–177° C.

Example 7 RPR110717

By working according to the procedure of Example 1, starting from 1.25 g of (3aR,4R, SR,7aR)-7,7-diphenyl-4-(2-methoxyphenyl)perhydro-4,5-isoindolediol and 0.95 g of [1-(2-dimethylaminoethyl)-3-indolyl]acetic acid, 1.4 g of (3aR,4R, SR,7aR)-7,7-diphenyl-4-(2-methoxyphenyl)-2-[(1-(2-dimethylaminoethyl)-3-indolyl)acetyl]perhydro-4,5-isoindolediol are obtained, melting at 210°–212° C.

[1-(2-Dimethylaminoethyl)-3-indolyl]acetic acid may be prepared according to the method of Andreani et al., Acta Pharm. Nord. 1991, 3(3), 125.

Example 8 RPR111271

By working according to the procedure of Example 1, starting from 0.5 g of (3aR,4R, SR,7aR)-7,7-diphenyl-4-(2-methoxyphenyl)perhydro-4,5-isoindolediol and 0.26 g of 3-(5-hydroxyindolyl)acetic acid, 0.20 g of (3aR,4R, SR,7aR)-7,7-diphenyl-4-(2-methoxyphenyl)-2[(5-hydroxy-3-indolyl)acetyl]perhydro-4,5-isoindolediol is obtained, melting at 230°–235° C.

The examples which follow illustrate the preparation of the racemic forms of the isoindole derivatives of general formula (I). Working by analogy with these examples, the corresponding perhydroisoindole derivatives of (3aR,4R, 5R,7aR) form may be prepared.

Example A RPR106891

To a solution of 0.42 g of (3aRS,4RS,5RS,7aRS)-7,7-diphenyl-4-(2-methoxyphenyl)perhydro-4,5-isoindolediol in 10 cm³ of dichloromethane is added 0.21 cm³ of diisopropylethylamine, followed by 0.23 g of 2-naphthylacetyl chloride in 5.5 cm³ of dichloromethane. After stirring at room temperature for 1 hour, 25 cm³ of water are added. The organic phase is separated off after settling, dried over magnesium sulphate and concentrated to dryness under reduced pressure (2.7 kPa). The residue is taken up in 50 cm³ of ethyl acetate, 3 cm³ of 1N aqueous hydrochloric acid and 40 cm³ of water. The organic phase is separated off after settling, dried over magnesium sulphate and concentrated to dryness under reduced pressure (2.7 kPa). The solid obtained is crystallized a first time in 5 cm³ of 2-propanol and then a second time in 5 cm³ of isopropyl ether. 0.3 g of (3aRS,4RS,5RS,7aRS)-7,7-diphenyl-4-(2-methoxyphenyl)-2-[(2-naphthyl)acetyl]perhydro-4,5-isoindolediol is obtained, melting at 188°–190° C.

2-Naphthylacetyl chloride is obtained from a mixture of 0.38 g of 2-naphthylacetic acid and 4 cm³ of thionyl chloride, which is brought to reflux for 20 minutes. After concentrating to dryness under reduced pressure (2.7 kPa), 0.41 g of an oil is obtained, which is used in the crude state in the subsequent syntheses.

Example B RPR106967

By working according to the procedure of Example A, starting from 0.62 g of (3aRS,4RS,5RS,7aRS)-7,7-diphenyl-4-(2-methoxyphenyl)perhydro-4,5-isoindolediol and 0.35 g of 1-naphthylacetyl chloride, 0.4 g of (3aRS,4RS,5RS, 7aRS)-7,7-diphenyl-4-(2methoxyphenyl)-2-[(1-naphthyl) acetyl]perhydro-4,5-isoindolediol is obtained, melting at 188°–190° C.

Example C RPR106966

By working according to the procedure of Example 1, starting from 0.83 g of (3aRS,4RS,5RS,7aRS)- methoxyphenyl)perhydro-4,5-isoindolediol and 0.43 g of 3-(5-fluoroindolyl)acetic acid, 0.8 g of (3aRS,4RS,5RS,7aRS)-7,7-diphenyl-4-(2-methoxyphenyl)-2-[(5-fluoro-3-indolyl)acetyl]perhydro-4,5-isoindolediol is obtained, melting at 248° C.

Example D RPR107091

By working according to the experimental procedure of Example 1, starting from 0.62 g of (3aRS,4RS,5RS,7aRS)-7,7-diphenyl-4-(2-methoxyphenyl)perhydro-4,5-isoindolediol and 0.34 g of 3-(5-methoxyindolyl)acetic acid, 0.78 g of (3aRS,4RS,5RS,7aRS)-7,7-diphenyl-4-(2-methoxyphenyl)-2[(5-methoxy-3-indolyl)acetyl]perhydro-4,5-isoindolediol is obtained, melting at 204°–206° C.

Example E RP 100949

To a solution of 4.5 g of (3aRS,4RS,5RS,7aRS)-7,7-diphenyl-4-(2-methoxyphenyl)perhydro-4,5-isoindolediol hydrochloride in 100 cm³ of dichloromethane, cooled to 0° C., are added 4.2 cm³ of triethylamine, followed by 2.4 g of (2-methoxyphenyl)acetic acid in 50 cm³ of dichloromethane. Stirring is carried out at room temperature for 90 minutes; the reaction mixture is washed with twice 10 cm³ of water, dried over magnesium sulphate and concentrated to dryness under reduced pressure (2.7 kPa). The crystallized solid is taken up with 100 cm³ of diisopropyl ether and then filtered, washed with 50 cm³ of saturated sodium bicarbonate solution and then with 50 cm³ of diisopropyl ether. 4.35 g of (3aRS,4RS,5RS,7aRS)-7,7-diphenyl-4-(2-methoxyphenyl)-2-(2-methoxyphenyl)acetylperhydro-4,5-isoindolediol are obtained, in the form of a light beige solid melting at 278° C.

(2-Methoxyphenyl)acetyl chloride is obtained from a mixture of 2.2 g of (2-methoxyphenyl)acetic acid and 20 cm³ of thionyl chloride, which is brought to reflux for 30 minutes. After concentrating to dryness under reduced pressure (2.7 kPa), 2.4 g of a yellow oil are obtained, which product is used in the crude state in the subsequent syntheses.

(3aRS,4RS,5RS,7aRS)-7,7-Diphenyl-4-(2-methoxyphenyl)perhydro-4,5-isoindolediol hydrochloride may be prepared in the following way:

To a solution of 5.15 g of (3aRS,4RS,5RS,7aRS)-7,7-diphenyl-4-(2-methoxyphenyl)-2-tert-butoxycarbonylperhydro-4,5-isoindolediol in 25 cm³ of dioxane is added at room temperature a solution of 25 cm³ of 6N hydrochloric dioxane. The reaction mixture is stirred for 1 hour at this temperature, followed by concentration to dryness under reduced pressure (2.7 kPa). The residue is washed with 20 cm³ of acetonitrile, filtered off and dried. 4.5 g of (3aRS,4RS,5RS,TaRS)-7,7-diphenyl-4-(2-methoxyphenyl)perhydro-4,5-isoindolediol hydrochloride are obtained, in the form of white crystals melting at a temperature greater than 300° C.

(3aRS,4RS,5RS,7aRS)-7,7-Diphenyl-4-(2-methoxyphenyl)-2-tert-butoxycarbonylperhydro-4,5-isoindolediol may be prepared in the following way:

To a suspension of 26.4 g of (3aRS,5RS,7aRS)-5-acetoxy-7,7-diphenyl-4-(2-methoxyphenyl)-2-tert-butoxycarbonylperhydro-4-isoindolone and 43.3 g of anhydrous cerium chloride in 265 cm³ of dry tetrahydrofuran is added dropwise, at room temperature with stirring, a suspension of 30.9 g of 2-methoxyphenylmagnesium bromide in 170 cm³ of dry tetrahydrofuran. The reaction mixture is stirred at room temperature for 24 hours, treated with 400 cm³ of saturated aqueous ammonium chloride solution, taken up in 1000 cm³ of ethyl acetate and then filtered over Celite. The organic phase is separated off after settling, dried over magnesium sulphate, filtered and concentrated to dryness under reduced pressure (2.7 kPa). The residue is chromatographed on a column of Merck silica gel (particle size 0.04–0.06 mm, diameter 7 cm, height 55 cm), eluting under a nitrogen pressure of 50 kPa with a mixture of cyclohexane and ethyl acetate (70/10 by volume) and collecting 250 cm³ fractions. Fractions 10 to 19 are combined and concentrated to dryness under reduced pressure (2.7 kPa). 18 g of (3aRS,4RS,5RS,7aRS)-7,7-diphenyl-4-(2-methoxyphenyl)-2-tert-butoxycarbonylperhydro-4,5-isoindolediol are obtained, in the form of white crystals melting at 229° C.

(3aRS,5RS,7aRS)-5-Acetoxy-7,7-diphenyl-2-tert-butoxycarbonylperhydro-4-isoindolone may be prepared in the following way:

To a suspension of 19 g of (3aRS,5RS,7aRS)-5-acetoxy-7,7-diphenylperhydro-4-isoindolone hydrochloride in 200 cm³ of dry dichloromethane are added, at a temperature in the region of 5° C., with stirring, 46.9 cm³ of triethylemine and 11.8 g of di-tert-butyl dicarbonate, followed by 0.3 g of 4-dimethylaminopyridine. The reaction mixture is stirred at room temperature for 24 hours and then washed with saturated aqueous sodium bicarbonate solution. The organic phase is separated off after settling, dried over magnesium sulphate, filtered and concentrated to dryness under reduced pressure (2.7 kPa). The residue is crystallized in 120 cm³ of diisopropyl ether. 21 g of (3aRS,5RS,7aRS)-5-Acetoxy-7,7-diphenylperhydro-4-isoindolone are obtained, in the form of white crystals melting at 213° C.

(3aRS,5RS,7aRS)-5-Acetoxy-7,7-diphenylperhydro-4-isoindolone hydrochloride may be prepared in the following way:

To a solution of 51.2 g of (3aRS,5RS,7aRS)-5-acetoxy-7,7-diphenyl-2-vinyloxycarbonylperhydro-4-isoindolone in 118 cm³ of dioxane is added, at room temperature, a solution of 394 cm³ of 5.2N hydrochloric dioxane. The reaction mixture is stirred for 1 hour at this temperature, followed by concentration to dryness under reduced pressure (2.7 kPa). The residue is recrystallized in 200 cm³ of boiling ethanol. 13.4 g of (3aRS,5RS,7aRS)-5-acetoxy-7,7-diphenylperhydro-4-isoindolone hydrochloride are obtained, in the form of white crystals melting at a temperature greater than 300° C.

(3aRS,5RS,7aRS)-5-Acetoxy-7,7-diphenyl-2-vinyloxycarbonylperhydro-4-isoindolone may be prepared in the following way:

To a solution of 58 g of (3aRS,5RS,7aRS)-5-acetoxy-2-benzyl-7,7-diphenylperhydro-4-isoindolinone in 580 cm³ of dry dichloromethane are added, at room temperature and with stirring, 13.6 cm³ of vinyl chloroformate. The reaction mixture is brought to the reflux of the solvent for one hour, cooled to room temperature and concentrated to dryness under reduced pressure (2.7 kPa). The residue is crystallized in 400 cm³ of a mixture of diisopropyl ether and petroleum ether (50/50 by volume). 51.4 g of (3aRS,5RS,7aRS)-5-acetoxy-7,7-diphenyl-2-vinyloxycarbonylperhydro-4-isoindolone are obtained, in the form of yellow crystals melting at 205°–210° C.

Example F RPR 106965

By working according to the procedure of Example 1, starting from 0.62 g of (3aRS,4RS,5RS,7aRS)-7,7-diphenyl-4-(2-methoxyphenyl)perhydro-4,5-isoindolediol and 0.31 g of 3-(N-methylindolyl)acetic acid, 0.55 g of (3aRS,4RS, 5RS,7aRS)-7,7-diphenyl-4-(2-methoxyphenyl)-2-[(N-methyl-3-indolyl)acetyl]perhydro4,5-isoindolediol is obtained, melting at 240° C.

Example G RPR107108

By working according to the procedure of Example 1, starting from 0.62 g of (3aRS,4RS,5RS,7aRS)-7,7-diphenyl-4-(2-methoxyphenyl)perhydro-4,5-isoindolediol and 0.30 g of (2-dimehylamino)phenylacetic acid, 0.47 g of (3aRS, 4RS,5RS,7aRS)-7,7-diphenyl-4-(2-methoxyphenyl)-2-[(2-dimethylaminophenyl)acetyl]perhydro-4,5-isoindolediol is obtained, melting at 250° C.

Example H RPR108329

By working according to the procedure of Example 1, starting from 0.62 g of (3aRS,4RS,5RS,7aRS)-7,7-diphenyl-4-(2-methoxyphenyl)perhydro-4,5-isoindolediol and 0.40 g of 2-(1-pyrrolidinyl)phenylacetic acid, 0.70 g of (3aRS,4RS, 5RS,7aRS)-7,7-diphenyl-4-(2-methoxyphenyl)-2-[(2-(1-pyrrolidinyl)phenyl)acetyl]perhydro-4,5-isoindolediol is obtained, melting at 236° C.

Example I RPR110166

To a solution of 1 g of (3aRS,4RS,5RS,7aRS)-7,7-diphenyl-4-(2-methoxyphenyl)-2-[(4-nitrophenyl)acetyl] perhydro-4,5-isoindolediol in 3.3 $cm^3$ of methanol, maintained at a temperature of 50° C., are added 33 $cm^3$ of water, 4.6 g of ammonium chloride and 2.2 g of zinc powder. The reaction mixture is brought to reflux for 30 minutes, cooled to room temperature and then washed with twice 50 $cm^3$ of dichloromethane. The organic phase is separated off after settling, dried over magnesium sulphate, filtered and concentrated to dryness under reduced pressure (2.7 kPa). The residue is taken up in 70 $cm^3$ of 1N hydrochloric acid. The organic phase is extracted with twice 50 $cm^3$ of ethyl acetate. The aqueous phase is basified with 1N sodium hydroxide and the organic phase is then extracted with 3 times 100 $cm^3$ of ethyl acetate. It is separated off after settling, dried over magnesium sulphate and concentrated to dryness under reduced pressure (2.7 kPa). The meringue-like product obtained is crystallized in 20 $cm^3$ of isopropyl ether. 0.71 g of (3aRS,4RS,5RS,7aRS)-7,7-diphenyl-4-(2-methoxyphenyl)-2-[(4-aminophenyl)acetyl]perhydro-4,5-isoindolediol is obtained, melting at 188° C.

(3aRS,4RS,5RS,7aRS)-7,7-Diphenyl-4-(2-methoxyphenyl)-2-[(4-nitrophenyl)acetyl]perhydro-4,5-isoindolediol may be prepared in the following way:

By working according to the procedure of Example 1, starting from 2 g of (3aRS,4RS,5RS,7aRS)-7,7-diphenyl-4-(2-methoxyphenyl)perhydro-4,5-isoindolediol and 0.92 g of 4-nitrophenylacetic acid, 1.25 g of (3aRS,4RS,5RS,7aRS)-7,7-diphenyl-4-(2-methoxyphenyl)-2-[(4-nitrophenyl) acetyl]perhydro-4,5-isoindolediol are obtained.

Example J RPR110169

By working according to the experimental procedure of Example 1, starting from 1 g of (3aRS,4RS,5RS,7aRS)-7, 7-diphenyl-4-(2-methoxyphenyl)perhydro-4,5-isoindolediol and 0.52 g of (4-dimehylamino)phenylacetic acid, 1.03 g of (3aRS,4RS,5RS,7aRS)-7,7-diphenyl-4-(2-methoxyphenyl)-2[(4-dimethylaminophenyl)acetyl]perhydro-4,5-isoindolediol are obtained, melting at 189° C.

The present invention also relates to the pharmaceutical compositions consisting of a product of general formula (I) or a salt when they exist, optionally combined with any other pharmaceutically compatible product, which may be inert or physiologically active. The compositions according to the invention may be used via the parenteral, oral, sublingual, rectal, topical, ocular or intranasal route, or as aerosols targeting the lungs.

The sterile compositions for parenteral adminstration which may in particular be used in the form of infusions are preferably aqueous or non-aqueous solutions, suspensions or emulsions. Water, propylene glycol, a polyethylene glycol, vegetable oils, in particular olive oil, injectable organic esters, for example ethyl oleate or other suitable organic solvents may be used as solvent or vehicle. These compositions may also contain adjuvants, in particular wetting, isotonicity, emulsifying, dispersing and stabilizing agents. The sterilization may be achieved in many ways, for example by aseptic filtration, by incorporating sterilizing agents into the composition, by irradiation or by heating. They may also be prepared in the form of sterile solid compositions which may be dissolved at the time of use into an injectable sterile medium.

The compositions for rectal administration are suppositories or rectal capsules, which contain, in addition to the active product, excipients such as cocoa butter, semi-synthetic glycerides or polyethylene glycols.

Tablets, pills, powders or granules may be used as solid compositions for oral administration. In these compositions, the active product according to the invention (optionally combined with another pharmaceutically compatible product) is mixed with one or more inert adjuvants or diluents, such as sucrose, lactose or starch. These compositions may also contain substances other than the diluents, for example a lubricating agent such as magnesium stearate.

Pharmaceutically acceptable emulsions, solutions, suspensions, syrups and elixirs containing inert diluents such as water or liquid paraffin may be used as liquid compositions for oral administration. These compositions may also contain substances other than the diluents, for example wetting, sweetening or flavouring products.

The compositions for topical administration may for example be creams, ointments or lotions.

The compositions for ocular administration may be instillations.

The compositions for intranasal administration may be pharmaceutically acceptable solutions or powders intended for droplet application or spraying.

The compositions may also be aerosols. For use in the form of liquid aerosols, the compositions may be stable sterile solutions or solid compositions dissolved at the time of use in apyrogenic sterile water, serum or any other pharmaceutically acceptable vehicle. For use in the form of dry aerosols intended to be inhaled directly, the active principle is finely divided and combined with a solid water-soluble vehicle or diluent having a particle size of 30 to 80 µm, for example dextran, mannitol or lactose.

In human therapy, the products according to the invention may be particularly useful in the treatment of painful and inflammatory spasmodic conditions of the respiratory pathways (asthma, asthmatiform bronchitis, bronchial hypersecretion, acute and chronic bronchitis, rhinitis, coughing, and tracheitis), of the digestive system (gastritis, gastralgia, diarrhoea, ulcerous colitis, irritable bowel syndrome, and Crohn's disease) and of the urinary system (urinary hyperreflexia and cystiris). They are also useful in the treatment of pain of traumatic, post-operative, menstrual or cephalic origin, in facial vascular neuralgia (cluster headache) and in the treatment of migraines. The new isoindole derivatives are also useful in the treatment of rheumatological inflammation, in the treatment of rheumatoid arthritis and in disorders due to the dysfunction of the immune system, in the treatment of dermatological inflammations such as psoriasis, herpes, urticaria, eczema, photodermatosis, burns and in dental or ocular inflammatory disorders and in the field of lachrymal secretions. The products according to the invention may also find an application in the treatment of neurologica diseases, Parkinson's disease, Alzeimer's disease, in the treatment of inflammatory and/or autoimmune and/or demyelinating diseases of the central and/or peripheral nervous system (multiple sclerosis, polyradiculonevritis, encephalopathy of viral origin etc.), in neurological syndromes related to a plasmatic extravasation (oedema of the spinal cord, cerebral oedema, etc.), related to breaching of the blood-brain barrier or in any spastic neurological syndrome (muscle-relaxant treatments). The products according to the invention may also be useful in the treatment of anxiety, psychosis, schizophrenia, or alternatively in the treatment of cardiovascular disorders such as hypotension. Another application may also be the treatment of gynaecological disorders, the treatment of disorders associated with poor growth regulation (dwarfism, hypotrophies which are secondary to chronic infant diseases, osteoporosis, and the development of grafts).

The doses depend upon the effect sought and on the duration of the treatment. For an adult, they are generally between 0.25 and 1500 mg per day in graded doses.

In general, the doctor will determine the dosage he considers to be the most suitable, depending on the age, the weight and all the other personal factors of the subject to be treated.

The example which follows, given without any limitation being implied, illustrates a composition according to the invention.

Example

Tablets of active product are prepared according to the usual technique, having the following composition:

| | |
|---|---|
| (3aR,4R,5R,7aR)-7,7-diphenyl-4-(2-methoxyphenyl)-2-[(3-indolyl)acetyl]perhydro-4,5-isoindolediol | 25 mg |
| starch | 83 mg |
| silica | 30 mg |
| magnesium stearate | 3 mg |

We claim:
1. A perhydroisoindole derivative of the formula (I) or salts thereof:

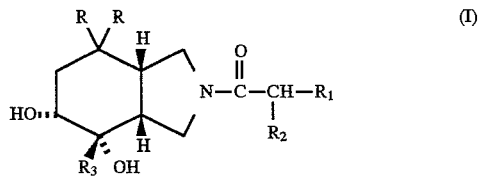

in which
the R groups are identical and represent phenyl radicals optionally substituted with a halogen atom or with a methyl radical in the 2- or 3- position,
$R_1$ represents a phenyl radical optionally substituted with one or more halogen atoms or hydroxyl, benzyloxy or alkyl radicals, said alkyl radicals being optionally substituted with halogen atoms or with amino, alkylamino or dialkylamino radicals, or said phenyl radical being optionally substituted with alkyloxy or alkylthio radicals, said alkyloxy, and alkylthio radicals being optionally substituted with hydroxyl, amino, alkylamino or dialkylamino radicals that are optionally substituted with phenyl, hydroxyl or amino, or said alkyloxy and alkylthio radicals being optionally substituted by dialkylamino radical whose alkyl portions form, with the nitrogen atom to which they are attached, a 5- to 6-membered heterocycle that may contain another hetero atom that is oxygen, sulphur or nitrogen, and said dialkylamino radical being optionally substituted with an alkyl, hydroxyl or hydroxyalkyl radical, or said phenyl radical being substituted with amino, alkylamino or dialkylamino radicals whose alkyl portions may form, together with the nitrogen atom to which they are attached, a heterocycle as defined above, or $R_1$ represents a cyclohexadienyl, naphthyl or indenyl radical, or a saturated or unsaturated mono- or polycyclic heterocyclic radical containing 5 to 9 carbon atoms and one or more hetero atoms chosen from oxygen, nitrogen or sulphur, and said cyclohexadienyl, naphthyl, or indenyl radicals being optionally substituted with a halogen atom or with an alkyl, alkyloxy, aminoalkyl, alkylaminoalkyl or dialkylaminoalkyl radical, $R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, and $R_3$ represents a phenyl radical optionally substituted in the 2-position with an alkyl or alkyloxy radical containing 1 or 2 carbon atoms, the alkyl and acyl radicals recited above being, with the exception of the recited heterocycles, straight or branched and containing 1 to 4 carbon atoms.

2. A perhydroisoindole derivative according to claim 1, wherein $R_1$ is a saturated or unsaturated mono- or polycyclic heterocyclic radical chosen from thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl or naphthyridinyl.

3. A perhydroisoindole derivative according to claim 1, which is (3aR,4R,5R,7aR)-7,7-diphenyl-4-(2-methoxyphenyl)-2-[(1 -(2-dimethylaminoethyl)-3-indolyl)acetyl]perhydro-4,5-isoindolediol.

4. A perhydroisoindole derivative according to claim 1, which is (3aR,4R,5R,7aR),7,7-diphenyl-4-(2-methoxyphenyl)-2-[(2-hydroxyphenyl)acetyl]perhydro-4,5-isoindolediol.

5. A perhydroisoindole derivative according to claim 1, which is (3aR,4R,5R,7aR)-7,7-diphenyl-4-(2-methoxyphenyl)-2-[(2-benzyloxyphenyl)acetyl]perhydro-4,5-isoindolediol.

6. A perhydroisoindole derivative according to claim 1, which is (3aR,4R,5R,7aR),7,7-diphenyl-4-(2-methoxyphenyl)-2-[(3-indolyl)acetyl]perhydro-4,5-isoindolediol.

7. A perhydroisoindole derivative according to claim 1, which is (3aR,4R,5R,7aR)-7,7-diphenyl-4-(2-methoxyphenyl)-2-[(5-hydroxy-3-indolyl)acetyl]perhydro-4,5-isoindolediol.

8. A process for preparing a perhydroisoindole derivative according to claim 1, comprising reacting an acid or a derivative of the acid of general formula:

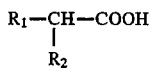

in which $R_1$ and $R_2$ are defined as in claim 1, with an isoindole derivative of general formula:

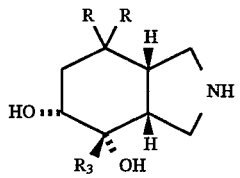

in which the symbols R and $R_3$ are defined as in claim 1, and optionally converting the product obtained to a salt.

9. A process for preparing a perhydroisoindole derivative of claim 1 wherein $R_1$ is a phenyl radical substituted with a hydroxyl, which comprises converting a perhydroisoindole derivative of claim 1 wherein $R_1$ is a phenyl radical substituted with a benzyloxy radical to said perhydroisoindole wherein $R_1$ is a phenyl radical substituted by hydroxy.

10. A process for preparing a perhydroisoindole derivative of claim 1 wherein $R_1$ is an amino-substituted phenyl radical, which comprises converting a perhydroisoindole derivative of claim 1, wherein $R_1$ is a phenyl radical substituted with a nitro radical to said perhydroisoindole wherein $R_1$ is an amino-substituted phenyl radical.

11. A method for treating diseases mediated by NK2 tachykinin receptors, comprising administering to a host in need of said treatment an effective amount of (3aRS,4RS, 5RS,7aRS) racemic derivatives of the perhydroisoindole derivatives according to claim 1.

12. A perhydroisoindole derivative of the formula (III) or a salt thereof:

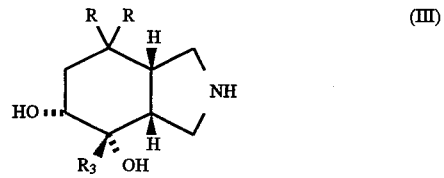

in which R and $R_3$ are defined as in claim 1.

13. A synergistic combination, comprising a perhydroisoindole derivative according to claim 1 and a product capable of antagonizing an NK1 receptor.

14. A pharmaceutical composition, comprising at least one derivative according to claim 1 together with one or more compatible and pharmaceutically acceptable diluents or adjuvants.

* * * * *

UNITED STATES PATENT AND TRADEMARK OFFICE
CERTIFICATE OF CORRECTION

PATENT NO. : 5,631,279
DATED : May 20, 1997
INVENTOR(S) : Andre CRESPO et al.

It is certified that error appears in the above-indentified patent and that said Letters Patent is hereby corrected as shown below:

On the Title Page, Item [57], in the Abstract, line 3, delete "08/448,402".

Claim 4, column 18, line 51, "),7,7" should read --)-7,7--.

Claim 6, column 18, line 59, "),7,7" should read --)-7,7--.

Signed and Sealed this

Nineteenth Day of May, 1998

Attest:

BRUCE LEHMAN

*Attesting Officer*     *Commissioner of Patents and Trademarks*